(12) United States Patent
Carbonelli et al.

(10) Patent No.: US 11,971,397 B2
(45) Date of Patent: Apr. 30, 2024

(54) GAS SENSING DEVICE FOR SENSING ONE OR MORE GASES IN A MIXTURE OF GASES

(71) Applicant: Infineon Technologies AG, Neubiberg (DE)

(72) Inventors: Cecilia Carbonelli, Munich (DE); Manuel Carro Dominguez, Munich (DE); Andrea Heinz, Munich (DE); Sebastian Schober, Munich (DE); Jianyu Zhao, Munich (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 383 days.

(21) Appl. No.: 17/361,853

(22) Filed: Jun. 29, 2021

(65) Prior Publication Data

US 2022/0011283 A1    Jan. 13, 2022

(30) Foreign Application Priority Data

Jul. 10, 2020    (EP) .................................. 20185318

(51) Int. Cl.
  *G01N 33/00*    (2006.01)
(52) U.S. Cl.
  CPC ..... *G01N 33/0034* (2013.01); *G01N 33/0063* (2013.01); *G01N 2033/0068* (2013.01)
(58) Field of Classification Search
  None
  See application file for complete search history.

(56) References Cited

FOREIGN PATENT DOCUMENTS

| DE | 19808197 A1 | 9/1999 |
| WO | 2016033186 A1 | 3/2016 |

OTHER PUBLICATIONS

Lipatov, Alexey et al., "Highly Selective Gas Sensor Arrays Based on Thermally Reduced Graphene Oxide", Nanoscale, vol. 5, 2013, pp. 5426-5434.*
Burgues, Javier et al., "Low Power Operation of Temperature-Modulated Metal Oxide Semiconductor Gas Sensors", Sensors, MDPI, Jan. 25, 2018, 15 pages.

(Continued)

*Primary Examiner* — Daniel S Larkin
(74) *Attorney, Agent, or Firm* — Slater Matsil, LLP

(57) ABSTRACT

A gas sensing device includes one or more chemo-resistive gas sensors; one or more heat sources, wherein the gas sensors are heated according to one or more first temperature profiles during the recovery phases and according to one or more second temperature profiles during the sense phases; a preprocessing processor for generating preprocessed signal samples; a feature extraction processor for extracting one or more feature values from the received preprocessed signal samples; and a gas concentration processor for creating a sensing result, wherein the gas concentration processor includes a classification processor for outputting a class decision value, wherein the classification processor is configured for outputting a confidence value, wherein the classification processor includes a first trained model based algorithm processor, wherein the gas concentration processor comprises a quantification processor for creating an estimation value, and wherein the quantification processor comprises a second trained model based algorithm processor.

20 Claims, 11 Drawing Sheets

(56) References Cited

OTHER PUBLICATIONS

Chen, Zhiyun et al., "Concentration Estimator of Mixed VOC Gases Using Sensor Array With Neural Networks and Decision Tree Learning", IEEE Sensors Journal, vol. 17, No. 6, Mar. 15, 2017, 9 pages.

Vergara, Alexander et al., "Optimized Feature Extraction for Temperature-Modulated Gas Sensors", Hindawi Publishing Corporation Journal of Sensors, Article ID 716316, Apr. 2009, 10 pages, doi:10.1155/2009/716316.

Wilson, Alphus Dan, "Review of Electronic-nose Technologies and Algorithms to Detect Hazardous Chemicals in the Environment", www.sciencediet.com, SciVerse ScienceDiet, Procedia Technology, Elsevier, vol. 1, Feb. 2012, pp. 453-463.

* cited by examiner

GAS SENSING DEVICE FOR SENSING ONE OR MORE GASES IN A MIXTURE OF GASES

This application claims the benefit of European Patent Application No. 20185318, filed on Jul. 10, 2020, which application is hereby incorporated herein by reference.

TECHNICAL FIELD

Embodiments relate to a gas sensing device for sensing one or more gases in a mixture of gases. Further embodiments relate to a method for operating such gas sensing device. More particular, the disclosure deals with the estimation of gas concentrations through the use of chemo-resistive gas sensors.

BACKGROUND

Literature on chemo-resistive gas sensors is generally limited to a simple model for proof of sensor functionality or costly data acquisition methodologies using geographically distributed sensor systems with impractical implementations. In order to distinguish between different gases, the use of selective physical gas filters or additional non-chemo-resistive gas sensors has been proposed. However, such use has a significant impact on the product sizes and cost.

SUMMARY

A gas sensing device for sensing one or more gases in a mixture of gases is provided. The gas sensing device comprises: one or more chemo-resistive gas sensors, wherein each of the gas sensors is configured for generating signal samples corresponding to a concentration of one of the one or more gases in the mixture of gases; one or more heat sources, wherein the one or more heat sources are controlled in such way that the gas sensors are each heated according to one or more temperature profiles; a preprocessing processor configured for receiving the signal samples from each of the gas sensors and for preprocessing the received signal samples in order to generate preprocessed signal samples for each of the gas sensors; a feature extraction processor configured for receiving the preprocessed signal samples and for extracting one or more feature values from the received preprocessed signal samples of each of the gas sensors based on characteristics of the received preprocessed signal samples of the respective gas sensor; and a gas concentration processor for creating for each of the gas sensors a sensing result, wherein the gas concentration processor comprises a classification processor configured for receiving a first group of the feature values comprising feature values for each of the gas sensors, wherein the classification processor is configured for outputting a class decision value for each of the gases, wherein each of the class decision values indicate whether the respective gas is present in the mixture of gases, wherein the classification processor is configured for outputting a confidence value for each of the class decision values, wherein each of the confidence values indicates a reliability of the respective class decision value, wherein the classification processor comprises a first trained model based algorithm processor and a first trained model for the first trained model based algorithm processor, wherein the feature values of the first group are fed to different inputs of the first trained model based algorithm processor, and wherein each of the class decision values and each of the confidence values are provided on different outputs of the first trained model based algorithm processor, wherein the gas concentration processor comprises a quantification processor configured for receiving a second group of the feature values comprising feature values for each of the gas sensors and for creating for each of the gases an estimation value, wherein each of the estimation values indicates a quantitative estimation of a concentration of the respective gas, wherein the quantification processor comprises a second trained model based algorithm processor and a second trained model for the second trained model based algorithm processor, wherein the feature values of the second group are fed to different inputs of the second trained model based algorithm processor, wherein the estimation values for the sensors are provided on different outputs of the second trained model based algorithm processor, and wherein the gas concentration processor is configured in such way that the sensing result for each of the gases depends on the estimation value for the respective gas, on the class decision value for the respective gas and on the confidence value for the respective gas.

The one or more chemo-resistive gas sensors may be graphene gas sensors or reduced graphene gas sensors, where the base material is functionalized with specific chemicals, e.g. with platinum (Pt), or manganese dioxide ($MnO_2$), so that each of the gas sensors is sensitive for gases, e.g. for nitrogen dioxide ($NO_2$), ozone ($O_3$) or carbon monoxide (CO). In doing so, the interaction between graphene sheets and absorbed gas analytes influences the electronic structure of the material depending on the mixture of gases, resulting in altered charge carrier concentration and changed electrical conductance.

In case of multi-gas sensing, a multi-gas sensor array comprising a plurality of chemo-resistive gas sensors having dissimilar selectivity may be used. Due to the different sensitivity towards various gas molecules, resistances of the gas sensors change in disparate patterns, making it possible to analyze complicated gas mixtures with one single sensor array.

According to embodiments, a gas sensing device has an improved detection mechanism, where the outputs of a classification processor and the outputs of a quantification processor are used to reduce cross-sensitivity, improve estimation accuracy for each single target gas in a mixture of gases.

A signal sample is a sequence consisting of time-discrete signal values, wherein the signal values are output by one of the gas sensors.

Each of the gas sensors may be heated by one or more heat sources. The heat sources may be electrically powered resistive heating elements or radiators emitting light, in particular with ultraviolet light. Each of the one or more heat sources is controlled according to one or more temperature profiles during operational phases. Each of the temperature profiles modulates a temperature of one or more of the gas sensors between a maximum temperature and a minimum temperature.

For example, according to one of the temperature profiles the temperature of the one or more heating elements may be pulsed between a maximum temperature and a minimum temperature The maximum temperature may be, for example, set to a value between 150° C. and 300° C., whereas the minimum temperature may be, for example, set to a value between 50° C. and 200° C.

In other embodiments, other temperature profiles, such as ramps, may be used.

The temperature modulation could be the same for all sensors or different for at least some of the sensors.

The temperature modulation improves repeatability and stability of the sensing results.

The term processor refers to an electronic device configured for specific task. A processor may comprise hardware or a combination of hardware and software. Different processors may share hardware components and/or software components.

The pre-processing processor is configured for suppressing and/or compensating of artifacts in the signal samples and/or noise in the signal samples and/or invalid signal samples due to malfunctioning gas sensors and/or errors in the signal samples due to drifts of the gas sensors in order to produce more reliable filtered signal samples.

The information extraction processor is configured for receiving the preprocessed signal samples and for extracting one or more feature values from the received preprocessed signal samples of each of the gas sensors based on characteristics of the received preprocessed signal samples of the respective gas sensor. The features may be based on dynamic characteristics of the signal samples. To this end, the pulsed nature of the responses of the gas sensors is leveraged and characteristics are extracted which rely on the dynamic evolution of the gas sensors.

The gas concentration processor is configured for creating for each of the gas sensors a sensing result. The sensing results may be alphanumeric terms, for example alphanumeric terms on a scale from "high" to "low". In particular, the terms of an air quality index system, for example terms of the European air quality index, may be used for outputting the sensing results. In other embodiments, the sensing results may be physical quantities, such as "4% by volume".

A trained model based algorithm processor is a processor, which is capable of machine learning. The machine learning is done in a preoperational training phase in which trained models are developed by comparing actual output values of the trained model based algorithm stage with desired output values of the trained model based algorithm stage for defined inputs of the trained model based algorithm stage. The trained models have a predefined structure, wherein a parametrization of the predefined structure is done during the training phase. The trained models comprise the learned content after the training phase is finished. In an operational phase for producing processing results, one or more of the trained models from the training phase are used to process their input data.

In the training phase the plurality of trained models can be established and afterwards stored at the gas sensing device. The trained models may differ in the structures and/or the parameters. During the operation phase the most appropriate trained model may be selected depending on the on the specific use-case.

The gas concentration processor comprises a classification processor configured for receiving a first group of the feature values comprising feature values for each of the gas sensors. The classification processor is configured for outputting a class decision value for each of the gases, wherein each of the class decision values indicate whether the respective gas is present in the mixture of gases. The classification processor is further configured for outputting a confidence value for each of the class decision values, wherein each of the confidence values indicates a reliability of the respective class decision value. Moreover, the classification processor comprises a first trained model based algorithm processor and a first trained model for the first trained model based algorithm processor, wherein feature values of the first group are fed to different inputs of the first trained model based algorithm processor, and wherein each of the class decision values and each of the confidence values are provided on different outputs of the first trained model based algorithm processor.

The first trained model of the classification processor is trained as a classification algorithm and at the same time as a confidence value calculating algorithm. The first trained model of the classification processor calculates the class decision value for each of the gases and the confidence value for each of the class decision values.

The gas concentration processor comprises a quantification processor configured for receiving a second group of the feature values comprising feature values for each of the gas sensors and for creating for each of the gases an estimation value, wherein each of the estimation values indicates a quantitative estimation of a concentration of the respective gas, wherein the quantification processor comprises a second trained model based algorithm processor and a second trained model for the second trained model based algorithm processor, wherein the feature values of the second group are fed to different inputs of the second trained model based algorithm processor, and wherein the estimation values for the gases are provided on different outputs of the second trained model based algorithm processor.

The second group of the feature values may comprise the same feature values or different feature values compared to the first group of feature values.

The second trained model of the classification processor is trained as a regression algorithm and calculates the estimation value for each of the gas sensors.

The gas concentration processor is configured in such way that the sensing result for each of the gases depends on the estimation value for the respective gas, on the class decision value for the respective gas and on the confidence value for the respective gas.

According to embodiments, the gas detection process is separated into two mechanisms, which process data from the same sensors. The outputs of the two mechanisms are then used for producing a final and more accurate sensing result. Specifically, a classifier is applied to the data to calculate whether a certain gas is present or not, and a regressor is used to quantify the concentration of the gas of interest from the same data. The outcome of these two mechanisms allows to remove cross-sensitivities and false alarms regarding a specific gas and at the same time to improve the accuracy on the gas predictions.

The gas sensing device can reflect real world scenarios, where, for example, gas mixtures are present which are causing cross-sensitivities in the sensor responses. In particular, the proposed gas sensing device is capable of distinguishing between different gases with reasonable accuracy, in particular between $NO_2$ and $O_3$, which are difficult to distinguish with chemo-resistive sensors.

The gas sensing device according to the disclosure addresses the intrinsic instability of chemo-resistive gas sensors. It uses robust algorithms and detection mechanisms, which can cope with calibration inaccuracies, drifts and other similar effects reliably and over a wide operating range. Moreover, the gas sensing device only takes a short time for reaching a stable response level.

The proposed gas sensing device provides an end to end solution for multi-gas adsorption sensors which is versatile, widely-applicable to multiple applications and uses cases (outdoor, indoor, health check, etc.) and can be embedded in a smart portable device. Specifically, an algorithm is used that works on continuous sensor readings, makes use of the transient information in the sensor responses and exhibits low complexity and limited memory requirements.

In particular, the gas sensing device may be used for air quality monitoring.

According to embodiments of the disclosure, the one or more gas sensors are alternately operated in recovery phases and in sense phases, wherein the one or more heat sources are controlled in such way that the gas sensors are each heated according to one or more first temperature profiles of the one or more temperature profiles during the recovery phases and according to one or more second temperature profiles of the one or more temperature profiles during the sense phases, wherein for each of the gas sensors a maximum temperature of the respective first temperature profile is higher than a maximum temperature of the respective second temperature profile.

Each of the one or more heat sources may be controlled according to one or more temperature profiles during the recovery phases and according to a second temperature profile during the sense phases, wherein a maximum temperature of the first temperature profile is higher than a maximum temperature of the second temperature profile.

For example, the temperature of the one or more heating elements may be pulsed between a first temperature during the recovery phases of the gas sensors and a second temperature during the sense phases of the gas sensors, wherein the first temperature is higher than the second temperature. The first temperature may be, for example, set to a value between 150° C. and 300° C., whereas the second temperature may be, for example, set to a value between 50° C. and 200° C.

The temperature modulation could be the same for all sensors or different for at least some of the sensors.

In order to improve repeatability and stability of the sensing results, at least some of the signal samples of each of the gas sensors may represent at least one of the recovery phases and at least one of the sense phases.

According to embodiments of the disclosure, the preprocessing processor is configured for executing a baseline calibration algorithm for the signal samples received from the gas sensors. Baseline manipulation is the transformation of a signal sample of one of the gas sensors into a relative resistance change with respect to sensor response to a reference analyte, wherein such sensor response is called a baseline. Synthetic air is a very common baseline as it is easily applicable and realistic in a real world scenario. The purpose of a baseline is to potentially create a more stable and reproducible sensing result by removing some of the drift caused by long term gas exposure and ageing of the sensor. As shown in Equation (1), subtracting the sensor response by its baseline Ro removes additive drift while division removes multiplicative drift. Using both operations combined results in the relative resistance change ΔR/Ro:

$$\Delta R/Ro = (R-Ro)/Ro \qquad (1)$$

According to embodiments of the disclosure, the preprocessing processor is configured for executing a filtering algorithm for the signal samples received from the gas sensors. The filtering algorithm may, for example, be implemented as a high pass filter or a noise filter. Such features further improve the accuracy of the sensing results.

According to embodiments of the disclosure, the feature extraction processor is configured for extracting from the received preprocessed signal samples a normalized sensor sensitivity ·d·R/Ra as one of the feature values for each of the gas sensors. The normalized sensor sensitivity ·d·R/Ro may be calculated according to Equation (1).

Using the normalized sensor sensitivities $\Delta R/R_0$ as feature values improves the accuracy of the sensing result.

According to embodiments of the disclosure, the feature extraction processor is configured for extracting from the received preprocessed signal samples a slope R'(t) of one of the preprocessed signal samples as one of the feature values for each of the gas sensors. The slope R'(t) or derivative may be calculated according to Equation (2):

$$R'(t) = \Delta R(t)/\Delta \qquad (2)$$

Using the slopes R'(t) as feature values improves the accuracy of the sensing result.

According to embodiments of the disclosure, the feature extraction processor is configured for extracting from the received preprocessed signal samples for each of the gas sensors a time correlation between a first of the preprocessed signal samples of the respective gas sensor and a second preprocessed signal sample of the respective gas sensor as one of the feature values for the respective gas sensor.

According to embodiments of the disclosure, the feature extraction processor is configured for extracting from the received preprocessed signal samples for each of the gas sensors a spatial correlation between one of the preprocessed signal samples of the respective gas sensor and one of the preprocessed signal sample of another of the gas sensors as one of the feature values for the respective gas sensor.

Given the dynamic behavior of the gas sensors, the availability of several transient in the sensor responses and the characteristic array structure with different functionalizations, it makes sense to introduce metrics which exploits such time and spatial properties. This can be achieved introducing a time autocorrelation function of the normalized sensor responses of the type (and its derivative)

$$R_\tau = \Sigma_{k=1}^n x_k y_k \qquad (3)$$

Where x and y indicate the normalized response at different moments in time (or, alternatively, their derivatives) and n is the window size being used to calculate the autocorrelation. Particularly:

$$x_k = \frac{\Delta R(k)}{R_o}; \; x_k = \Delta R(k+\tau)/R_0 \qquad (4)$$

Similarly, the correlation among the different gas sensors should also be exploited with a spatial correlation matrix of the type:

$$R_s[r, p] = \frac{1}{n}\sum_{i=1}^n x_{i,r} x_{i,p} \qquad (5)$$

According to embodiments of the disclosure, the first trained model based algorithm processor is implemented as a first artificial neural network.

According to embodiments of the disclosure, the second trained model based algorithm processor is implemented as a second artificial neural network.

An artificial neural network is a parameterized statistic model, in which a number of logistic regressions are combined non-linearly. Such systems "learn" to perform tasks by considering examples, generally without being programmed with any task-specific rules. A neural network is based on a collection of connected nodes called artificial neurons. Each connection can transmit a signal from one artificial neuron to another. An artificial neuron that receives a signal can process it and then signal additional artificial neurons connected to it. A model predefines the structure of the nodes or the hyperparameters of a neural network and the parameters of the connections are found by training the neural network. Structure and the corresponding parameters form a trained model for the respective neural network.

According to embodiments of the disclosure, for each of the gases the sensing result for the respective gas is the estimation value for the respective gas, wherein the class decision value for the respective gas and the confidence value for the respective gas are fed to one of the inputs of the second trained model based algorithm processor in order to make the estimation value for each of the gases dependent on the class decision value for the respective gas and on the confidence value for the respective gas.

In such embodiments, the first group of the feature values may be fed to different inputs of the first trained model based algorithm processor of the classification processor and the class decision value for each of the gases and the confidence value for each of the gases may be output at different outputs of the first trained model based algorithm processor of the classification processor. The second group of the feature values and the class decision value for each of the gases and the confidence value for each of the gases may be fed to different inputs of the second trained model based algorithm processor of the gas concentration processor and the estimation values for each of the gases may be output at different outputs of the second trained model based algorithm processor of the gas concentration processor.

According to embodiments of the disclosure, the gas concentration processor comprises a post processing processor configured for estimating the sensing result for each of the sensors depending on the estimation value for the respective sensor, on the class decision value for the respective sensor and on the confidence value for the respective sensor based on one or more predefined rules.

In such embodiments, the first group of the feature values may be fed to different inputs of the first trained model based algorithm processor of the classification processor and the class decision value for each of the gases and the confidence value for each of the gases may be output at different outputs of the first trained model based algorithm processor of the classification processor. The second group of the feature values may be fed to different inputs of the second trained model based algorithm processor of the gas concentration processor and the estimation values for each of the gases may be output at different outputs of the second trained model based algorithm processor of the gas concentration processor. The estimation values for each of the gases, the class decision value for each of the gases and the confidence value for each of the gases may be forwarded to the post processing processor which outputs the sensing results for each of the gases depending on the estimation value for the respective gas, the class decision value for the respective gas and the confidence value for the respective gas.

An exemplary rule could be, that, in case that the quantification processor estimates a specific concentration of a specific gas and the classification processor estimates that the specific gas does not exist in the mixture of gases with high confidence, that the sensing result for the specific gas is set to "zero" or to "unknown".

According to embodiments of the disclosure, the post processing processor is configured for re-calibration of each of the sensors using the estimation value for the respective sensor, the class decision value for the respective sensor and the confidence value for the respective sensor. In particular, sensor drift may be compensated. This can be done in cases, in which the classification processor estimates that, with high confidence, one specific gas does not exist in the mixture of gases.

According to embodiments of the disclosure, the gas concentration processor comprises a feature normalization processor configured for receiving the second group of the feature values, the class decision values for each of the gases and the confidence values for each of the gases, wherein the feature normalization processor is configured for calculating a normalized form of the second group of the feature values using the class decision values for each of the gases and the confidence values for each of the gases, wherein the feature normalization processor is configured for transmitting the second group of the feature values in the normalized form to the quantification processor.

In such embodiments, predictions from the classification processor may initiate a new calculation of the sensors baseline and therefore a re-normalization of the features from the pre-processing processor. This re-normalization can improve the gas concentration estimations by providing the quantification processor with drift-compensated feature values.

According to embodiments of the disclosure the second trained model based algorithm processor comprises for each of the gases a convolutional processor, wherein the second trained model based algorithm processor comprises a dense layer processor, wherein at least a portion of the second group of the feature values is fed to each of the convolutional processors, wherein each of the convolutional processors is configured for creating for each of the gases a preliminary estimation value, wherein each of the preliminary estimation values indicates a quantitative preliminary estimation of a concentration of the respective gas, wherein the preliminary estimation value for each of the gases, the class decision value for each of the gases and the confidence value for each of the gases are input to the dense layer processor, wherein the dense layer processor creates the estimation value for each of the gases based on the preliminary estimation values, based on the class decision values and based on the confidence values.

The advantage of the approach is that each of the separate convolutional processors can first separately learn the most relevant features values for the respective gas and the class-related information is only subsequently incorporated as an input to the dense layer processor. Thus, the dense layer processor can then still exploit cross-correlation across gases and the information from the classification processor. This approach can improve the sensing results.

In such embodiments, the estimation value for each of the gases may be used as the sensing results for each of the gases.

In a further aspect of the disclosure, a method for operating a gas sensing device for sensing one or more gases in a mixture of gases, which comprises one or more chemoresistive gas sensors is disclosed. The method comprises using each of the gas sensors for generating signal samples corresponding to a concentration of one of the one or more gases in the mixture of gases; using one or more heat sources for heating each of the gas sensors according to one or more temperature profiles; using a preprocessing processor for receiving the signal samples from each of the gas sensors and for preprocessing the received signal samples in order to generate preprocessed signal samples for each of the gas sensors; using a feature extraction processor for receiving the preprocessed signal samples and for extracting one or more feature values from the received preprocessed signal samples of each of the gas sensors based on characteristics of the received preprocessed signal samples of the respective gas sensor; using a classification processor of a gas concentration processor for receiving a first group of the feature values comprising feature values for each of the gas sensors, wherein the classification processor is configured for outputting a class decision value for each of the gases, wherein each of the class decision values indicate whether the respective gas is present in the mixture of gases, wherein the classification processor is configured for outputting a confidence value for each of the class decision values, wherein each of the confidence values indicates a reliability of the respective class decision value, wherein the classification processor comprises a first trained model based algorithm processor and a first trained model for the first trained model based algorithm processor, wherein feature values of the first group are fed to different inputs of the first trained model based algorithm processor, wherein each of the class decision values and each of the confidence values are provided on different outputs of the first trained model based algorithm processor; and using a quantification processor of the gas concentration processor for receiving a second group of the feature values comprising feature values for each of the gas sensors and for creating for each of the gases an estimation value, wherein each of the estimation values indicates a quantitative estimation of a concentration of the respective gas, wherein the quantification processor comprises a second trained model based algorithm processor and a second trained model for the second trained model based algorithm processor, wherein the feature values of the second group are fed to different inputs of the second trained model based algorithm processor, and wherein the estimation values for the gases are provided on different outputs of the second trained model based algorithm processor; and using the gas concentration processor in such way that the sensing result for each of the gases depends on the estimation value for the respective gas, on the class decision value for the respective gas and on the confidence value for the respective gas.

BRIEF DESCRIPTION OF THE DRAWINGS

Preferred embodiments of the invention are subsequently discussed with respect to the accompanying drawings, in which.

Figure 1:
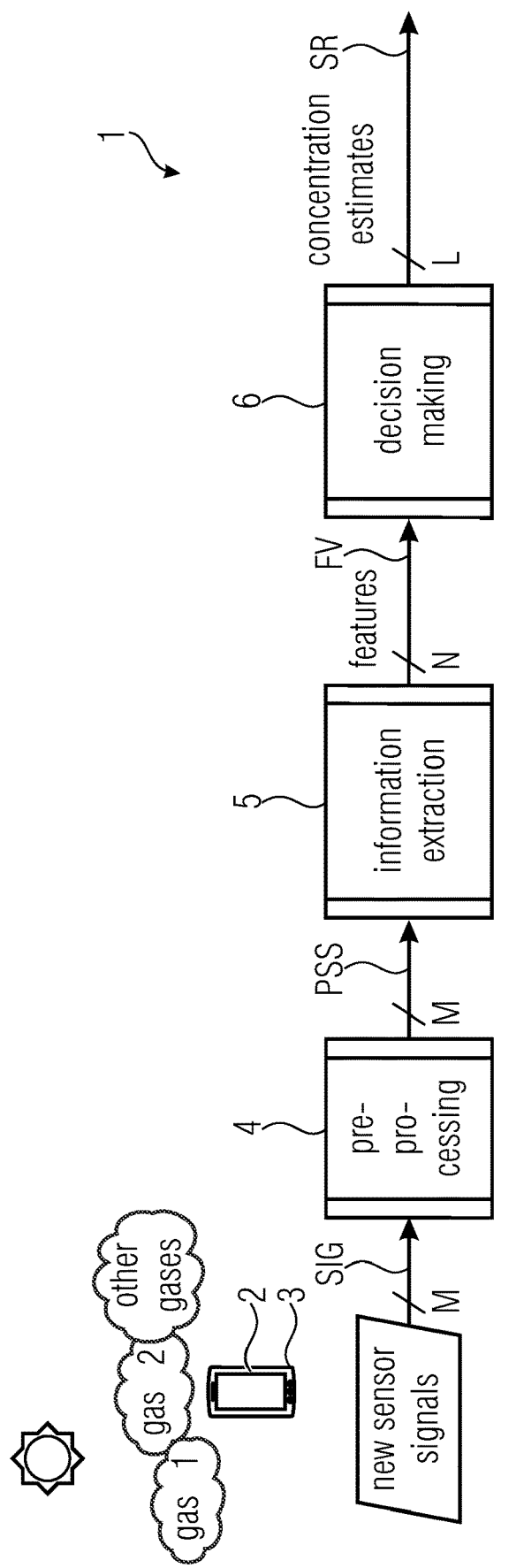
FIG. 1 shows a schematic view of an exemplary embodiment of a gas sensing device according to prior art, which comprises four chemo-resistive gas sensors.

Equal or equivalent elements or elements with equal or equivalent functionality are denoted in the following description by equal or equivalent reference numerals.

DETAILED DESCRIPTION OF ILLUSTRATIVE EMBODIMENTS

In the following description, a plurality of details is set forth to provide a more thorough explanation of embodiments of the present disclosure. However, it will be apparent to those skilled in the art that embodiments of the present disclosure may be practiced without these specific details. In other instances, well-known structures and devices are shown in block diagram form rather than in detail in order to avoid obscuring embodiments of the present disclosure. In addition, features of the different embodiments described hereinafter may be combined with each other, unless specifically noted otherwise.

FIG. 1 shows a schematic view of an exemplary embodiment of a gas sensing device 1 according to prior art, which comprises four chemo-resistive gas sensors.

The gas sensing device 1 comprises one or more chemo-resistive gas sensors 2, wherein each of the gas sensors 2 is configured for generating signal samples SIG corresponding to a concentration of one of the one or more gases in the mixture of gases, wherein the one or more heat sources 3 are controlled in such way that each of the gas sensors 2 are heated according to one or more temperature profiles; a preprocessing processor 4 configured for receiving the signal samples SIG from each of the gas sensors 2 and for preprocessing the received signal samples SIG in order to generate preprocessed signal samples PSS for each of the gas sensors 2; a feature extraction processor 5 configured for receiving the preprocessed signal samples PSS and for extracting one or more feature values FV from the received preprocessed signal samples PSS of each of the gas sensors 2 based on characteristics of the received preprocessed signal samples PSS of the respective gas sensor 2; and a gas concentration processor 6 for creating for each of the gas sensors 2 a sensing result SR. The gas concentration processor 6 is configured as a regressor 6.

Figure 2:
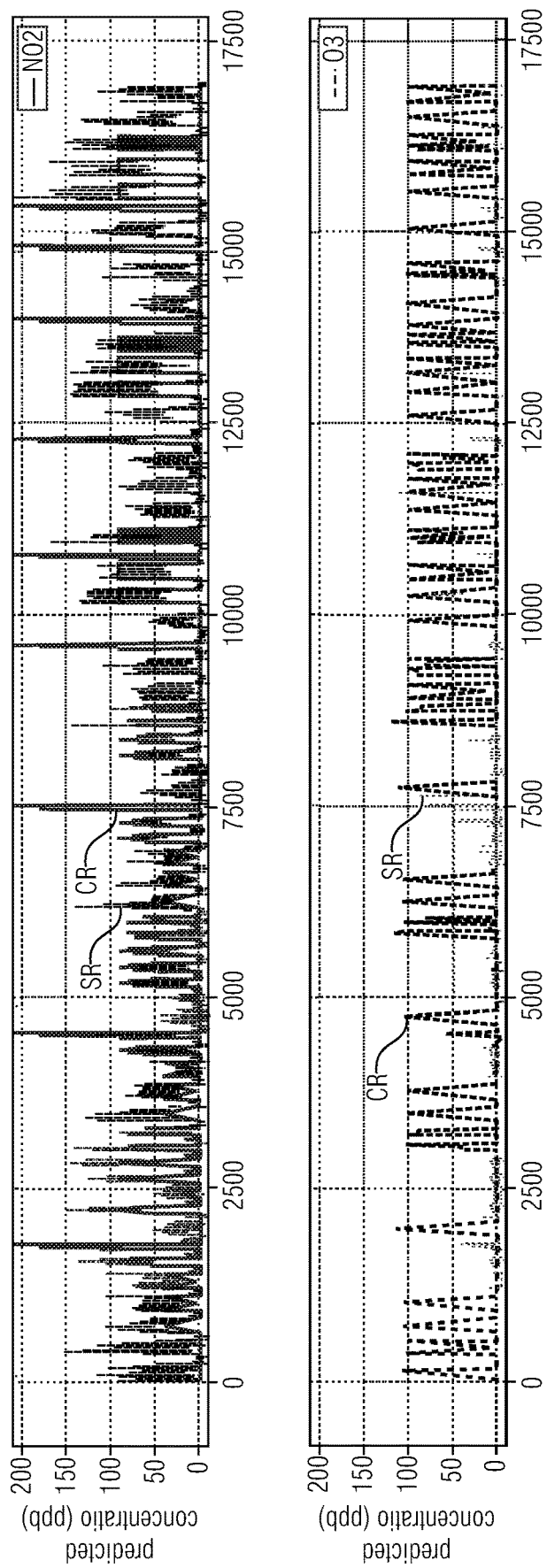
FIG. 2 shows a prediction performance of the exemplary embodiment of a gas sensing device according to prior art.

FIG. 2 shows a prediction performance of the exemplary embodiment of a gas sensing device 1 according to prior art. The drawbacks of the traditional approach shown in FIG. 1 are illustrated in FIG. 2, where the concentration estimates SR (lighter curves) of the regressor 6 for the target gases, in this example $NO_2$ and $O_3$, are plotted against their correct labels CR (darker curves). Here it is seen that severe cross-sensitivity occurs when only a single gas is present, which is reflected by the erroneously detected second gas. In this example, this is particularly evident in the $NO_2$ predictions, which carry several 'false alarms' or 'interference' from the $O_3$ pattern.

Figure 3:
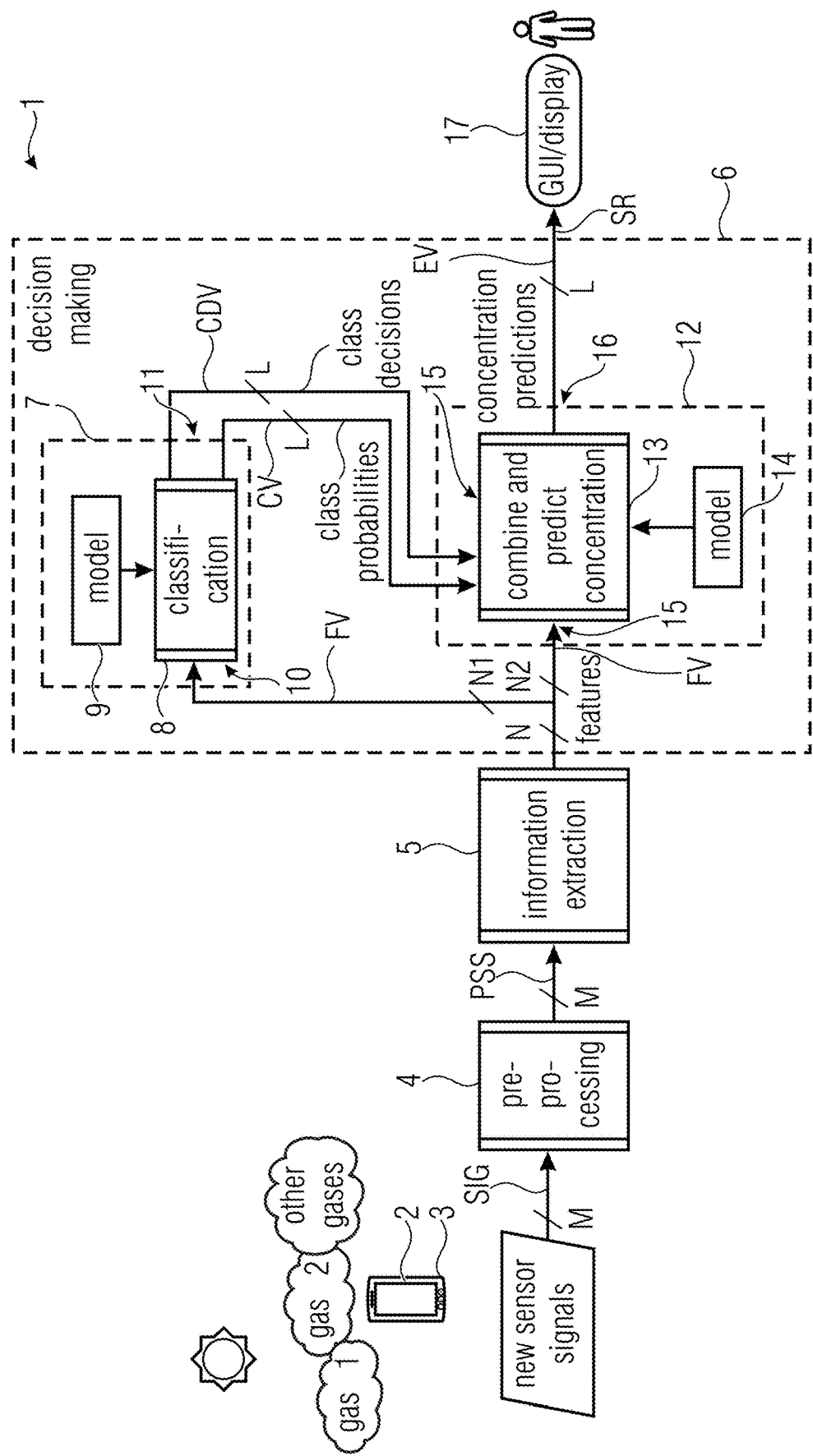
FIG. 3 shows a schematic view of a first exemplary embodiment of a gas sensing device according to the disclosure, which comprises four chemo-resistive gas sensors.

FIG. 3 shows a schematic view of a first exemplary embodiment of a gas sensing device 1 according to the disclosure, which comprises four chemo-resistive gas sensors 2.

The gas sensing device 1 is configured for sensing one or more gases in a mixture of gases. The gas sensing device 1 comprises one or more chemo-resistive gas sensors 2, wherein each of the gas sensors 2 is configured for generating signal samples SIG corresponding to a concentration of one of the one or more gases in the mixture of gases; one or more heat sources 3, wherein the one or more heat sources 3 are controlled in such way that the gas sensors 2 each are heated according to one or more temperature profiles FTP; a preprocessing processor 4 configured for receiving the signal samples SIG from each of the gas sensors 2 and for preprocessing the received signal samples SIG in order to generate preprocessed signal samples PSS for each of the gas sensors 2; a feature extraction processor 5 configured for receiving the preprocessed signal samples PSS and for extracting one or more feature values FV from the received preprocessed signal samples PSS of each of the gas sensors 2 based on characteristics of the received preprocessed signal samples PSS of the respective gas sensor 2; and a gas concentration processor 6 for creating for each of the gas sensors 2 a sensing result SR, wherein the gas concentration processor 6 comprises a classification processor 7 configured for receiving a first group of the feature values FV comprising feature values FV for each of the gas sensors 2, wherein the classification processor 7 is configured for outputting a class decision value CDV for each of the gases, wherein each of the class decision values CDV indicate whether the respective gas is present in the mixture of gases, wherein the classification processor 7 is configured for outputting a confidence value CV for each of the class decision values CDV, wherein each of the confidence values CV indicates a reliability of the respective class decision value CDV, wherein the classification processor 7 comprises a first trained model based algorithm processor 8 and a first trained model 9 for the first trained model based algorithm processor 8, wherein feature values FV of the first group are fed to different inputs 10 of the first trained model based algorithm processor 8, and wherein each of the class decision values CDV and each of the confidence values CV are provided on different outputs 11 of the first trained model based algorithm processor 8, wherein the gas concentration processor 6 comprises a quantification processor 12 configured for receiving a second group of the feature values FV comprising feature values FV for each of the gas sensors 2 and for creating for each of the gases an estimation value EV, wherein each of the estimation values EV indicates a quantitative estimation of a concentration of the respective gas, wherein the quantification processor 12 comprises a second trained model based algorithm processor 13 and a second trained model 14 for the second trained model based algorithm processor 13, wherein the feature values FV of the second group are fed to different inputs 15 of the second trained model based algorithm processor 13, wherein the estimation values EV for the gases are provided on different outputs 16 of the second trained model based algorithm processor 13, and wherein the gas concentration processor 6 is configured in such way that the sensing result SR for each of the gases depends on the estimation value EV for the respective gas, on the class decision value CDV for the respective gas and on the confidence value CV for the respective gas.

The gas sensing device 1 shown in FIG. 3 comprises M sensors 2, wherein each of the M sensors 2 produces a signal sample SIG so that M signal samples SIG are produced at the same time. M may be any positive integer, for example four. The preprocessing processor 4 receives the M signal samples SIG and produces for each of the M signal samples SIG a preprocessed signal sample PSS so that M preprocessed signal samples PSS are produced at the same time. The feature extraction processor 5 receives the M preprocessed signal samples PSS and produces for each of the M preprocessed signal samples PSS one or more feature values FV so that N feature values FV are produced at the same time. N is an integer, which is usually equal to or greater than M.

The first group of feature values FV, which comprises N1 feature values FV, is fed to the classification processor 7. The classification processor 7 produces for each of the L gases to be detected a class decision value CDV and a confidence value CV so that L class decision value CDV and L confidence values CV are produced at the same time. The L class decision values CDV and the L confidence values CV are fed together with the second group of feature values FV, which comprises N2 feature values FV, to the quantification processor 12. The quantification processor 12 produces from the L class decision value CDV, from the L confidence values CV and from the second group of feature values FV L estimation values EV, wherein each of the estimation values EV indicates a quantitative estimation of a concentration of one of the L gases to be detected. L may be an integer being smaller than, equal to or greater than M.

In the example of FIG. 3 each of the estimation values EV represents the sensing result SR for one of the gases to be sensed. The sensing results SR may be displayed on a display 17.

In some embodiments, the gas sensing device comprise a pre-processing processor 4, where artifacts, noise, malfunctioning sensors and drift are suppressed or compensated, an feature extraction processor 5, where the pre-processed sensor responses PSS are transformed and 'coded' into feature values FV with the appropriate reduced dimensionality and at the same time the most informative content, wherein possible feature values FV are the normalized sensitivity, the derivative or slope, time and spatial correlation across sensors and a quantification processor 12, where a continuous estimation of the gas concentration is provided resorting to a regression algorithm, which will be preferably implemented as a feedforward neural network (FFNN), a recurrent neural network (RRN) or a convolutional neural network (CNN).

To improve the performance of the sensing device 1 in the presence of a gas mixture, it is proposed to feed the raw data SIG, PSS and/or feature values FV extracted from them to a classification processor 7, which decides, for example, whether $O_3$ or $NO_2$ is present in a gas mixture. The classification processor 7 could be a feedforward network or a simple convolutional neural network, depending on the trade-off between accuracy and hardware requirements, e.g. power, memory, size, material costs. The classification processor 7 also provides the confidence levels (prediction probabilities, {Pa}) for the different classes.

The information CDV and CV of the classification processor 7 and the information EV of the quantification processor 12 are combined to improve the final predictions SR. This combination could be a 'hard combination' happening at the output of the quantification processor 12, that is, in post-processing, or a 'soft combination' happening at the input of the quantification processor 12 or within the quantification processor 12.

It has to be noted that the classification processor 7 can process directly the raw data SIG and PSS; the same feature values FV or a part of the feature values FV that are also sent to the quantification processor 12; and/or feature values FV, which are not sent to the quantification processor 12.

Finally, an enhancement of the mechanism in FIG. 3 can be devised where a (non-recursive) classification processor 7 receives a feedback in the form of the predicted concentration values EV from the quantification processor 12. Based on a threshold, the predicted concentration EV of a gas influences the prediction of the classification processor 7 for the next input.

According to embodiments of the disclosure, the one or more gas sensors 2 are alternately operated in recovery phases RP and in sense phases SP, wherein the one or more heat sources 3 are controlled in such way that the gas sensors 2 are each heated according to one or more first temperature profiles FfP of the one or more temperature profiles FTP, STP during the recovery phases RP and according to one or more second temperature profiles STP of the one or more temperature profiles FfP, STP during the sense phases SP, and wherein for each of the gas sensors 2 a maximum temperature of the respective first temperature profile FTP is higher than a maximum temperature of the respective second temperature profile STP.

According to embodiments of the disclosure, the preprocessing processor 4 is configured for executing a baseline calibration algorithm for the signal samples SIG received from the gas sensors 2.

According to embodiments of the disclosure, the preprocessing processor 4 is configured for executing a filtering algorithm for the signal samples SIG received from the gas sensors 2.

According to embodiments of the disclosure, the feature extraction processor 5 is configured for extracting from the received preprocessed signal samples PSS a normalized sensor sensitivity as one of the feature values FV for each of the gas sensors 2.

According to embodiments of the disclosure, the feature extraction processor 5 is configured for extracting from the received preprocessed signal samples PSS a slope of one of the preprocessed signal samples PSS as one of the feature values FV for each of the gas sensors 2.

According to embodiments of the disclosure, the feature extraction processor 5 is configured for extracting from the received preprocessed signal samples PSS for each of the gas sensors 2 a time correlation between a first of the preprocessed signal samples PSS of the respective gas sensor 2 and a second preprocessed signal sample PSS of the respective gas sensor 2 as one of the feature values FV for the respective gas sensor 2.

According to embodiments of the disclosure, the feature extraction processor 5 is configured for extracting from the received preprocessed signal samples PSS for each of the gas sensors 2 a spatial correlation between one of the preprocessed signal samples PSS of the respective gas sensor 2 and one of the preprocessed signal sample PSS of another of the gas sensors 2 as one of the feature values FV for the respective gas sensor 2.

According to embodiments of the disclosure, the first trained model based algorithm processor 8 is implemented as a first artificial neural network.

According to embodiments of the disclosure, the second trained model based algorithm processor 13 is implemented as a second artificial neural network.

According to embodiments of the disclosure, for each of the gases, the sensing result SR for the respective gas is the estimation value EV for the respective gas, wherein the class decision value CDV for the respective gas and the confidence value CV for the respective gas are fed to one of the inputs 15 of the second trained model based algorithm processor 13 in order to make the estimation value EV for each of the gases dependent on the class decision value CDV for the respective gas and on the confidence value CV for the respective gas.

In a further aspect, the disclosure refers to a method for operating a gas sensing device 1 for sensing one or more gases in a mixture of gases, wherein the gas sensing device 1 comprises one or more chemo-resistive gas sensors 2, wherein the method comprises using each of the gas sensors 2 for generating signal samples SIG corresponding to a concentration of one of the one or more gases in the mixture of gases; using one or more heat sources 3 for heating each of the gas sensors 2 according to one or more temperature profiles FTP, STP; using a preprocessing processor 4 for receiving the signal samples SIG from each of the gas sensors 2 and for preprocessing the received signal samples SIG in order to generate preprocessed signal samples PSS for each of the gas sensors 2; using a feature extraction processor 5 for receiving the preprocessed signal samples PSS and for extracting one or more feature values FV from the received preprocessed signal samples PSS of each of the gas sensors 2 based on characteristics of the received preprocessed signal samples PSS of the respective gas sensor 2; using a classification processor 7 of a gas concentration processor 6 for receiving a first group of the feature values FV comprising feature values FV for each of the gas sensors 2, wherein the classification processor 7 is configured for outputting a class decision value CDV for each of the gases, wherein each of the class decision values CDV indicate whether the respective gas is present in the mixture of gases, wherein the classification processor 7 is configured for outputting a confidence value CV for each of the class decision values CDV, wherein each of the confidence values CV indicates a reliability of the respective class decision value CDV, wherein the classification processor 7 comprises a first trained model based algorithm processor 8 and a first trained model 9 for the first trained model based algorithm processor 8, wherein feature values FV of the first group are fed to different inputs 10 of the first trained model based algorithm processor 8, and wherein each of the class decision values CDV and each of the confidence values CV are provided on different outputs 11 of the first trained model based algorithm processor 8; using a quantification processor 12 of the gas concentration processor 6 for receiving a second group of the feature values FV comprising feature values FV for each of the gas sensors 2 and for creating for each of the gases an estimation value EV, wherein each of the estimation values EV indicates a quantitative estimation of a concentration of the respective gas, wherein the quantification processor 12 comprises a second trained model based algorithm processor 13 and a second trained model 14 for the second trained model based algorithm processor 13, wherein the feature values FV of the second group are fed to different inputs 15 of the second trained model based algorithm processor 13, wherein the estimation values EV for the gases are provided on different outputs 16 of the second trained model based algorithm processor 13; and using the gas concentration processor 6 in such way that the sensing result SR for each of the gases depends on the estimation value EV for the respective gas, on the class decision value CDV for the respective gas and on the confidence value CV for the respective gas.

Figure 4:
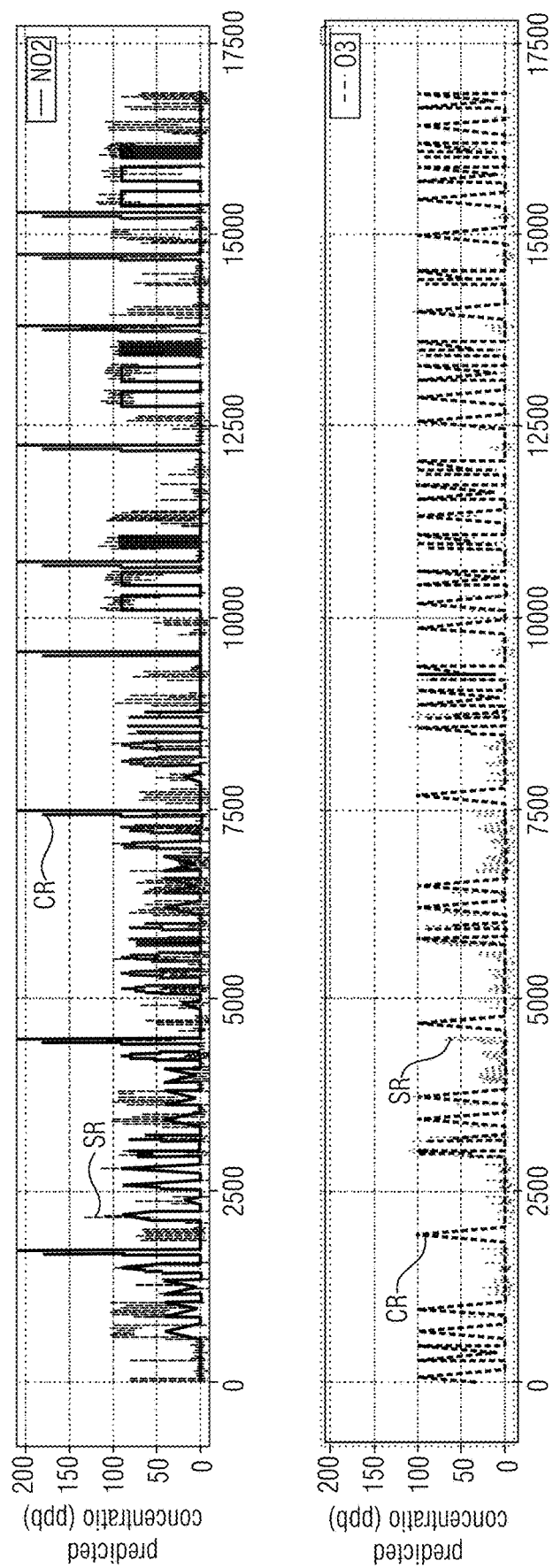
FIG. 4 shows a prediction performance of the first embodiment of a gas sensing device according to the disclosure.

FIG. 4 shows a prediction performance of the first embodiment of a gas sensing device 1 according to the disclosure, where the sensing results SR (lighter curves) of the quantification processor 13 for the target gases, in this example $NO_2$ and $O_3$, are plotted against their correct labels CR (darker curves). It is seen that prediction performance is significantly improved over the conventional one shown in FIG. 2. In particular, the cross-sensitivity is reduced and the predictions are more accurate.

Figure 5:
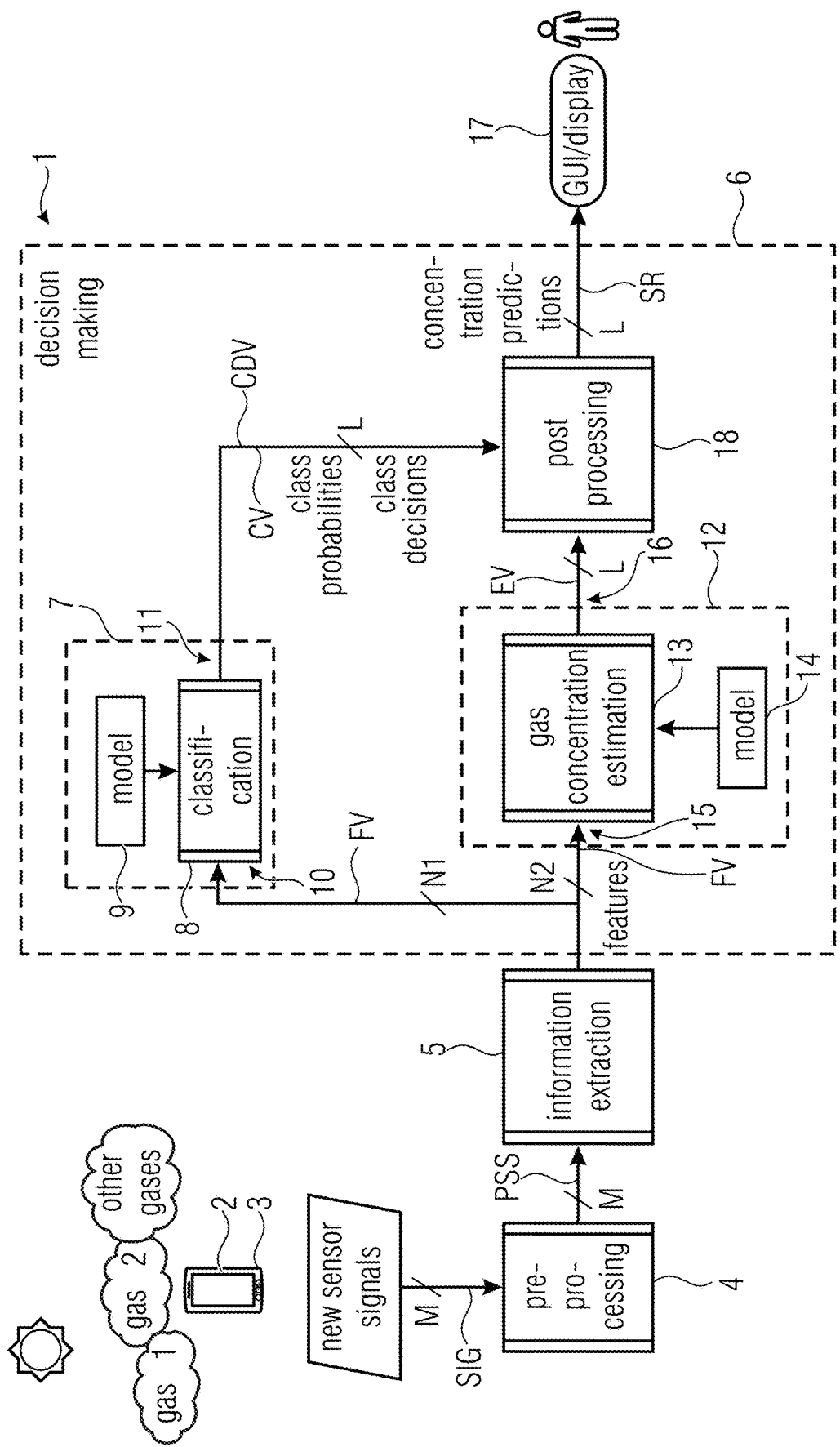
FIG. 5 shows a schematic view of a second exemplary embodiment of a gas sensing device according to the disclosure, which comprises four chemo-resistive gas sensors.

FIG. 5 shows a schematic view of a second exemplary embodiment of a gas sensing device 1 according to the disclosure, which comprises four chemo-resistive gas sensors. The second embodiment is based on the first embodiment so below the differences are discussed.

According to embodiments of the disclosure, the gas concentration processor 6 comprises a post processing processor 18 configured for estimating the sensing result SR for each of the sensors 2 depending on the estimation value EV for the respective sensor 2, on the class decision value CDV for the respective sensor 2 and on the confidence value CV for the respective sensor 2 based on one or more predefined rules.

In the second embodiment, the first group of feature values FV, which comprises N1 feature values FV, is fed to the classification processor 7. The classification processor 7 produces for each of the L gases to be detected a class decision value CDV and a confidence value CV so that L class decision value CDV and L confidence values CV are produced at the same time. The second group of feature values FV, which comprises N2 feature values FV, is fed to the quantification processor 12. The quantification processor 12 produces from the second group of feature values FV L estimation values EV, wherein each of the estimation values EV indicates a quantitative estimation of a concentration of one of the L gases to be detected. The L class decision values CDV and the L confidence values CV are fed together with the L estimation values EV to the post processing processor 18. The post processing processor 18 produces from the L class decision value CDV, from the L confidence values CV and from the L estimation values EV L sensing results L using predefined rules.

For example, the following rules may be applied:

Discard unreliable gas predictions: If the maximum probability across all target classes (for instance, $NO_{2/O3}$) is below a certain threshold, then the corresponding estimate output at the quantification processor 12 is ignored (and not sent to the display 17).

Overrule the quantification processor 12 with the decision of the classification processor 7: If the classification processor 7 has identified one gas only, for example $O_3$ or $NO_2$, then set to zero the prediction of the quantification processor 12 for the other gas(es), in this case $NO_2$ or $O_3$ respectively. If the classifier has identified only a class probability of $NO_2$ and $O_3$, which is below a threshold, set $O_3$ and $NO_2$ to zero.

The rules above have been established as the classification processor 7 can normally be considered more reliable than the quantification processor 12 with similar amount of parameters but that also needs to quantify a gas concentration with ppb level accuracy.

It is clear that more rules can be derived depending on the expected output of the gas sensing device 1 and on the availability of a finer classification especially in scenarios with gas mixtures containing a higher number of gases.

According to embodiments of the disclosure, the post processing processor 18 is configured for re-calibration of each of the sensors 2 using the estimation value EV for the respective sensor 2, the class decision value CDV for the respective sensor 2 and the confidence value CV for the respective sensor 2.

Figure 6:
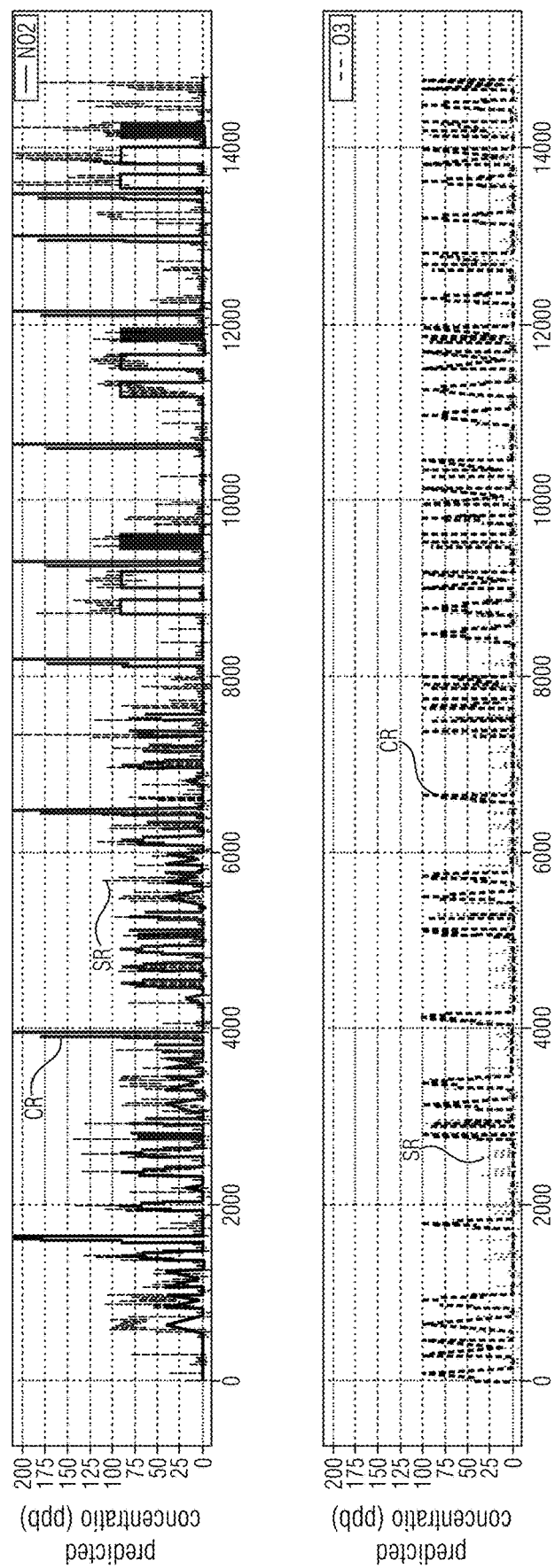
FIG. 6 shows a prediction performance of the second embodiment of a gas sensing device according to the disclosure.

FIG. 6 shows a prediction performance of the second embodiment of a gas sensing device according to the disclosure, where the sensing results SR (lighter curves) of the quantification processor 13 for the target gases, in this example $NO_2$ and $O_3$, are plotted against their correct labels CR (darker curves). It is seen that prediction performance is significantly improved over the conventional one shown in FIG. 2. In particular, the cross-sensitivity is reduced and the predictions are more accurate.

Figure 7:
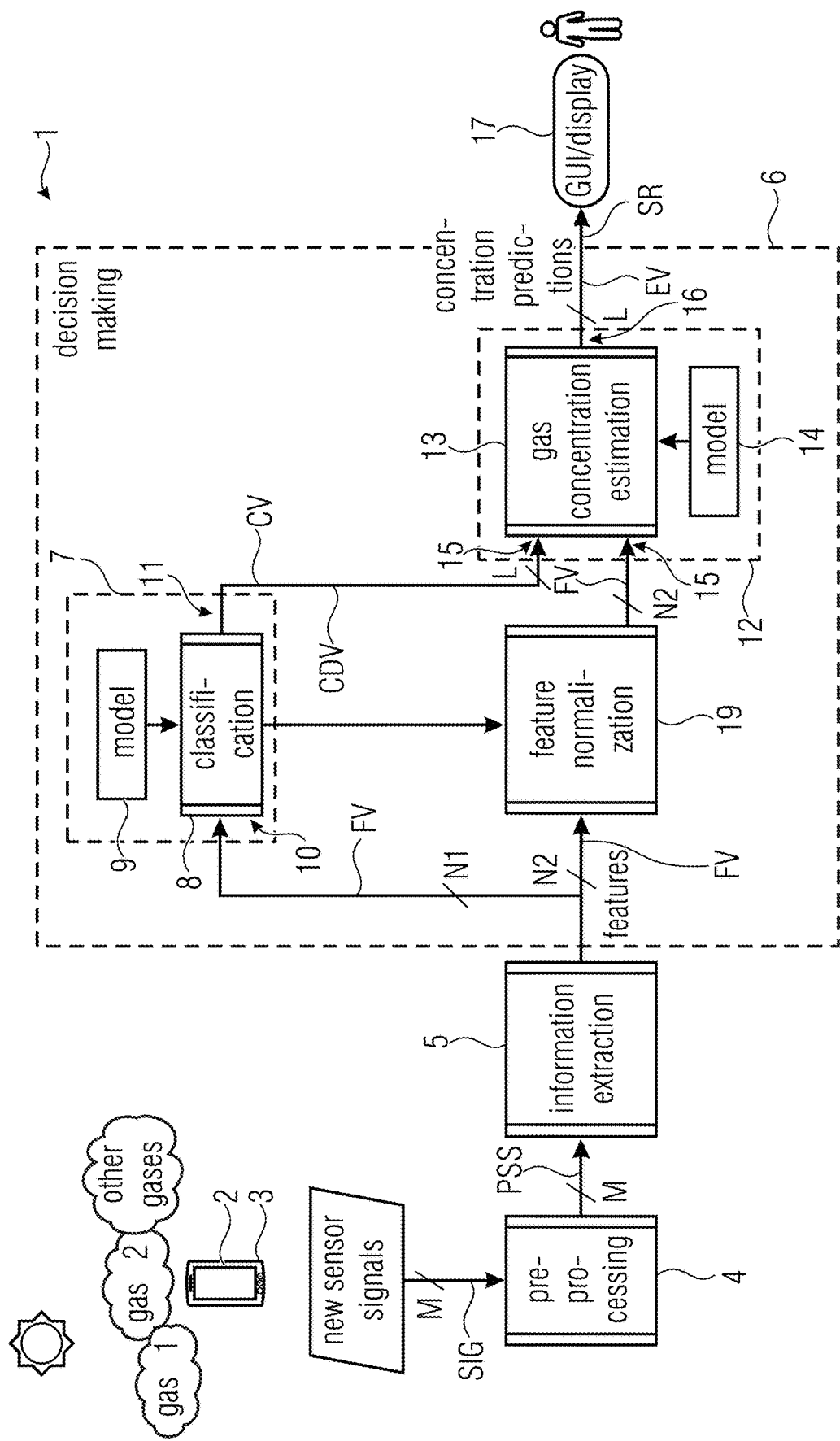
FIG. 7 shows a schematic view of a third exemplary embodiment of a gas sensing device according to the disclosure, which comprises four chemo-resistive gas sensors.

FIG. 7 shows a schematic view of a third exemplary embodiment of a gas sensing device 1 according to the disclosure, which comprises four chemo-resistive gas sensors. The third embodiment is based on the first embodiment so what below only the differences are discussed.

According to embodiments of the disclosure, the gas concentration processor 6 comprises a feature normalization processor 19 configured for receiving the second group of the feature values FV, the class decision values CDV for each of the gases and the confidence values CV for each of the gases, wherein the feature normalization processor 19 is configured for calculating a normalized form of the second group of the feature values FV using the class decision values CDV for each of the gases and the confidence values CV for each of the gases, wherein the feature normalization processor 19 is configured for transmitting the second group of the feature values FV in the normalized form to the quantification processor 12.

The first group of feature values FV, which comprises N1 feature values FV, is fed to the classification processor 7. The classification processor 7 produces for each of the L gases to be detected a class decision value CDV and a confidence value CV so that L class decision value CDV and L confidence values CV are produced at the same time. The second group of feature values FV, which comprises N2 feature values FV, is forwarded to the feature normalization processor 19, which normalizes the feature values FV of the second group of feature values FV.

The L class decision values CDV and the L confidence values CV are fed together with the N normalized feature values FV of the second group to the quantification processor 12. The quantification processor 12 produces from the L class decision value CDV, from the L confidence values CV and from the normalized feature values FV of the second group L estimation values EV, wherein each of the estimation values EV indicates a quantitative estimation of a concentration of one of the L gases to be detected.

In order to compensate for sensor drift, the embodiment shown in FIG. 3 can be extended to the embodiment shown in FIG. 7 so that certain classifier predictions CV, CDV initiate a new calculation of the sensors baseline and therefore a re-normalization of the feature values FV from the feature extraction processor 5. This re-normalization can improve the gas concentration estimations SR by providing the quantification processor 12 with drift-compensated feature values FV.

Figure 8:
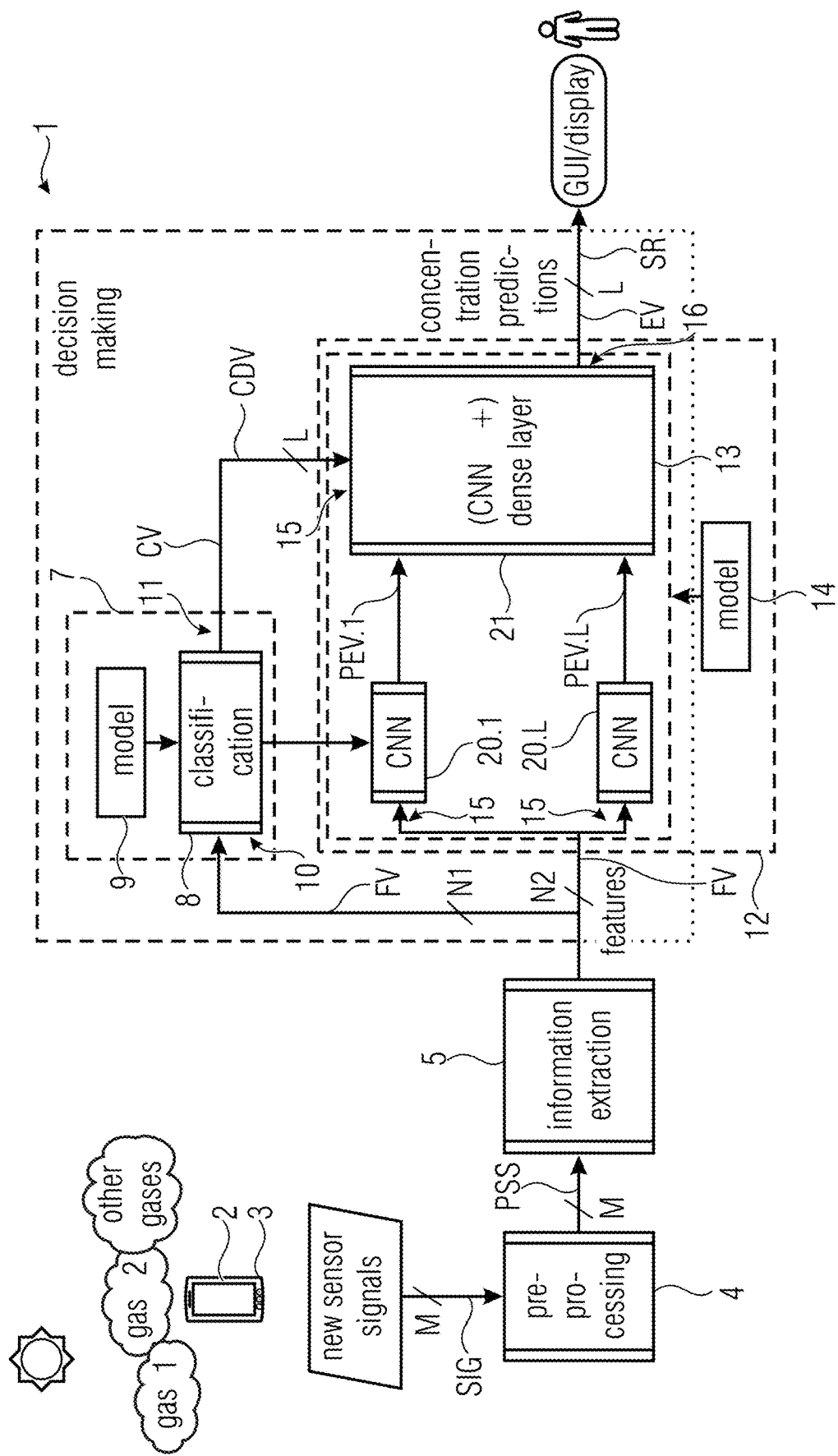
FIG. 8 shows a schematic view of a fourth exemplary embodiment of a gas sensing device according to the disclosure, which comprises four chemo-resistive gas sensors.

FIG. 8 shows a schematic view of a fourth exemplary embodiment of a gas sensing device 1 according to the disclosure, which comprises four chemo-resistive gas sensors. The fourth embodiment is based on the first embodiment so below the differences are discussed.

According to embodiments of the disclosure, the second trained model based algorithm processor 13 comprises for each of the gases a convolutional processor 20, wherein the second trained model based algorithm processor 13 comprises a dense layer processor 21, wherein at least a portion of the second group of the feature values FV is fed to each of the convolutional processors 20, wherein each of the convolutional processors 20 is configured for creating for each of the gases a preliminary estimation value PEV, wherein each of the preliminary estimation values PEV indicates a quantitative preliminary estimation of a concentration of the respective gas, wherein the preliminary estimation value PEV for each of the gases, the class decision value CDV for each of the gases and the confidence value CV for each of the gases are input to the dense layer processor 21, wherein the dense layer processor 21 creates the estimation value EV for each of the gases based on the preliminary estimation values PEV, based on the class decision values CDV and based the confidence values CV.

The first group of feature values FV, which comprises N1 feature values FV, is fed to the classification processor 7. The classification processor 7 produces for each of the L gases to be detected a class decision value CDV and a confidence value CV so that L class decision value CDV and L confidence values CV are produced at the same time.

The second group of feature values FV, which comprises N2 feature values FV, is forwarded to each of the L2 convolutional processors 20, which produces for each of the L gases a preliminary estimation value PEV.

The L class decision values CDV and the L confidence values CV are fed together with the preliminary estimation values PEV to the quantification processor 12. The quantification processor 12 produces from the L class decision value CDV, from the L confidence values CV and from the preliminary estimation values PEV L estimation values EV, wherein each of the estimation values EV indicates a quantitative estimation of a concentration of one of the L gases to be detected.

The fourth approach is also based on a 'soft combination' of the outputs CV, CDV of the classification processor 7 in the regression mechanism of the quantification processor 12. Here, the outputs CV, CDV of the classification processor 7 are incorporated as an auxiliary inputs in the middle of the regressor flow. More specifically, L parallel and separate convolution processors are used first for the different gases. The outputs of these parallel streams are then 'fused' with the outputs CV, CDV of the classification processor 7 prior to the dense layer processor 21.

The advantage of the approach is that each of the separate convolutional processors 20 can first separately learn the most relevant feature values for the respective target gas and the class-related information CV, CDV is only subsequently incorporated as an input to the dense layer processor 21. Thus, the dense layer processor 21 can then still exploit cross-correlation across gases and the information CV, CDV from the classification processor 7. This approach is also the one with the best performance, and, due to the use of convolutional blocks, also the one with the highest complexity and memory requirements.

Figure 9:
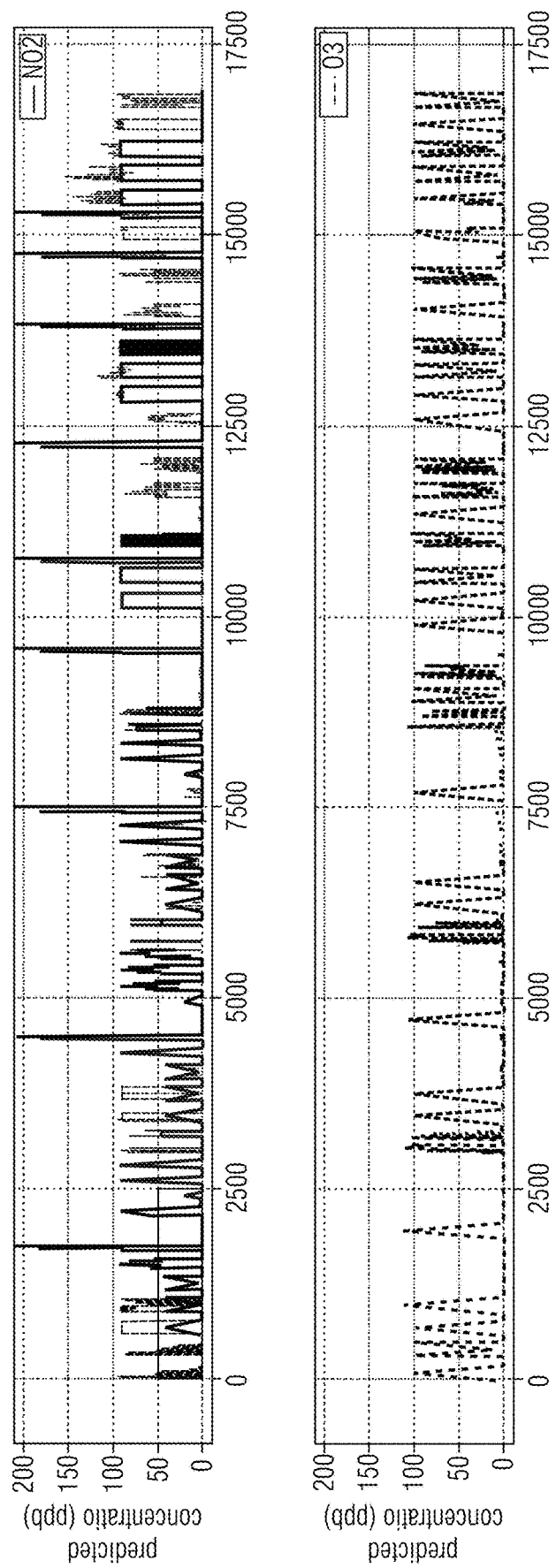
FIG. 9 shows a prediction performance of the fourth embodiment of a gas sensing device according to the disclosure.

FIG. 9 shows a prediction performance of the fourth embodiment of a gas sensing device according to the disclosure, where the sensing results SR (lighter curves) of the quantification processor 13 for the target gases, in this example $NO_2$ and $O_3$, are plotted against their correct labels CR (darker curves). It is seen that prediction performance is significantly improved over the conventional one shown in FIG. 2. In particular, the cross-sensitivity is reduced and the predictions are more accurate.

The prediction performance of the fourth embodiment is the best one but has a higher complexity as ca. 600o parameters need to be optimized versus 1400 at the first embodiment and 1200 for the second embodiment.

Figure 10:
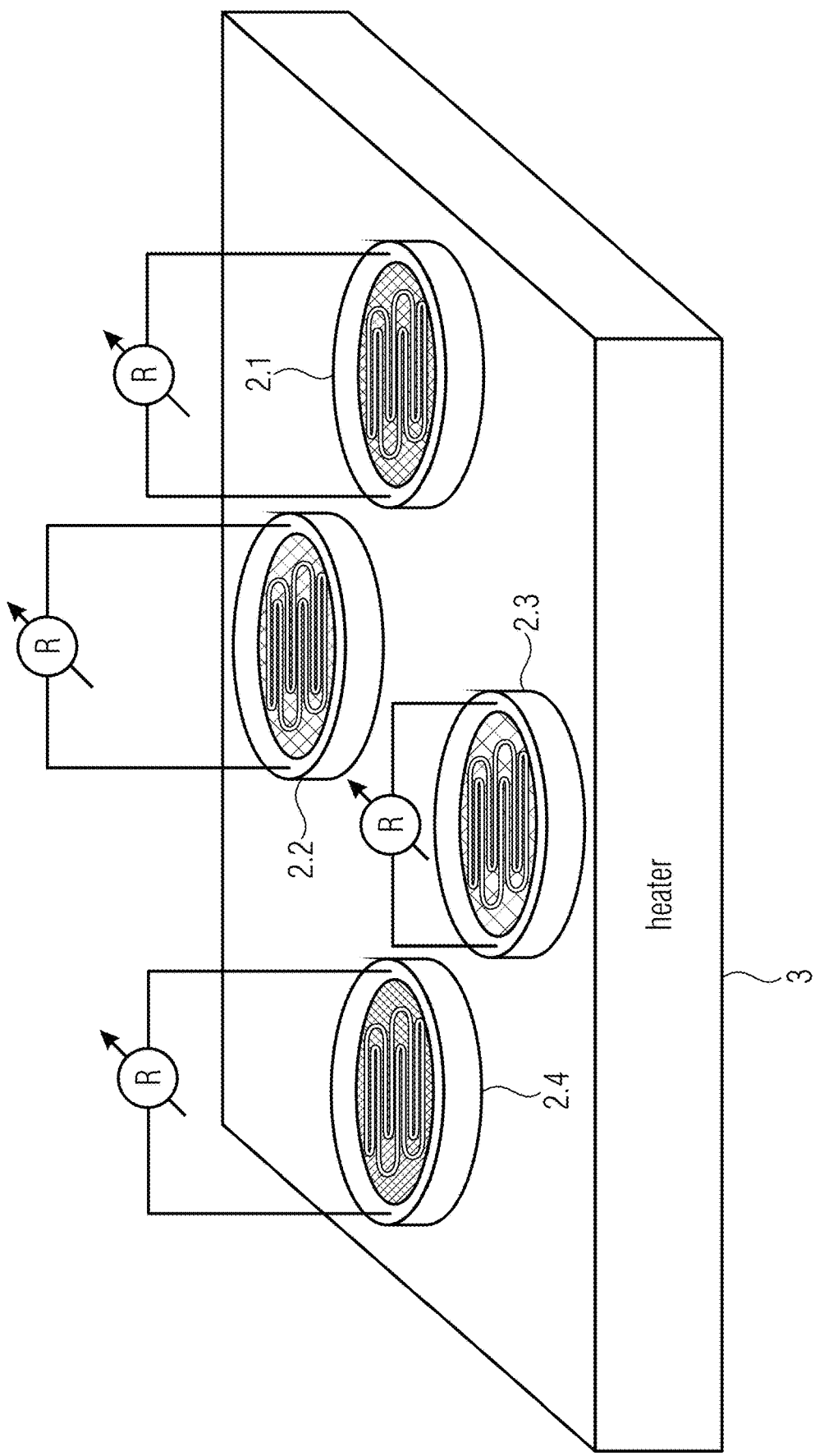
FIG. 10 shows an exemplary graphene multi-gas sensor array according to the disclosure.
Figure 11:
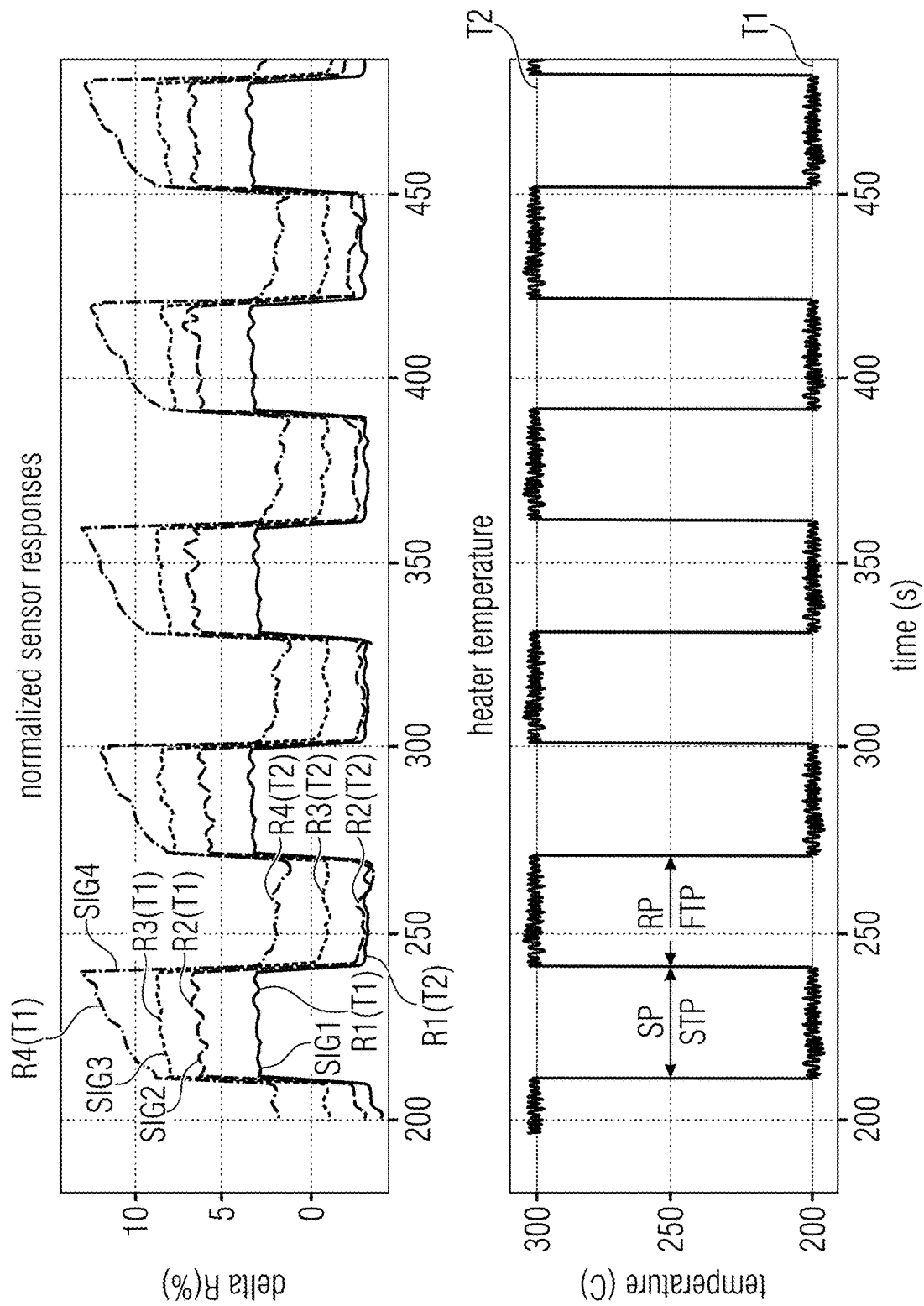
FIG. 11 illustrates exemplary normalized sensor responses and heater temperatures over time.

FIG. 10 shows an exemplary graphene multi-gas sensor array according to the disclosure. Each sensor 2.1, 2.2, 2.3 and 2.4 in the array is heated by a heat source 3, whose temperature is being pulsed between first temperature T1 during a recovery phase and a second temperature T2 during sense phase (see FIG. 11). In other embodiments, the sensors 2.1, 2.2, 2.3 and 2.4 in the array are heated by a plurality of heat sources 3. For example, each of the sensors 2.1, 2.2, 2.3 and 2.4 could be heated individually by one heat source of the plurality of the heat sources. The result of these controlled temperature oscillations is a more dynamic behavior of the signal samples SIG1, SIG2, SIG3, and SIG4 as shown in FIG. 11, which is exploited by the gas sensing device 1.

Several implementations of temperature pulsing mechanism are possible. For example, the temperature modulation could be the same for all sensors 2.1, 2.2, 2.3 and 2.4 or different in order to better exploit the different functionalizations of the base material and to improve gas separability. Similarly, multiple heater controls can be used (one for each sensor 2.1, 2.2, 2.3 and 2.4) or, alternatively, a single heater control in time division multiplexing with different applied voltages so as to obtain sensor specific temperature values.

The sensors 2.1, 2.2, 2.3 and 2.4 form a multi-gas sensor array, where a base material consisting of graphene is functionalized with different chemicals (e.g. Pd, Pt, and $MnO_2$) for dissimilar selectivity. The interaction between graphene sheets and absorbed gas analytes would influence the electronic structure of the material, resulting in altered charge carrier concentrations and changed electrical conductance. Meanwhile, due to different sensitivity towards various gas molecules resistances of the sensors 2.1, 2.2, 2.3 and 2.4 also change in disparate patterns, making it possible to analyze complicated gas mixtures with one single sensor array.

Figure ii illustrates exemplary normalized signal samples SIG1, SIG2, SIG3 SIG4 for the chemo-resistive gas sensors 2.1, 2.2, 2.3, 2.4 and temperature profiles FTP, STP over time. In the particular example of FIG. 11 two temperatures profiles FTP, STP are chosen: A first temperature profile FTP for sensing the sensor resistances and for recovering the sensors surface and desorb adsorbed gas molecules at a constant temperature of 300° C. in a recovery phase RP and a second temperature profile STP for sensing the sensor resistances at a constant temperature of 200° C. during a sense phase SP. Therefore, not only static features like absolute or relative sensor resistance changes can be monitored, but also dynamic features like e.g. the slope of the sense phase SP at 200° C., which reflects the gas adsorption over time. According to FIG. 11, the signal samples SIG1, SIG2, SIG3 SIG4 are produced during the sense phases SP and during the recovery phases RP. However, in other embodiments, the signal samples SIG1, SIG2, SIG3 SIG4 may be produced during the sense phases SP only. Additional temperature steps and pulse modes are also possible, as long as they contribute additional information or features to the signal samples SIG1, SIG2, SIG3 and SIG4 like gas adsorption/reaction at a certain temperature or temperature ramp.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

The above described is merely illustrative, and it is understood that modifications and variations of the arrangements and the details described herein will be apparent to others skilled in the art. It is the intent, therefore, to be limited only by the scope of the impending claims and not by the specific details presented by way of description and explanation above.

What is claimed is:

1. A gas sensing device for sensing one or more gases in a mixture of gases, the gas sensing device comprising:

one or more chemo-resistive gas sensors, wherein each of the gas sensors is configured for generating signal samples corresponding to a concentration of one of the one or more gases in the mixture of gases;

one or more heat sources, wherein the one or more heat sources are controlled in such a way that the one or more chemo-resistive gas sensors are each heated according to one or more temperature profiles;

a preprocessing processor configured for receiving the signal samples from each of the gas sensors and for preprocessing the received signal samples in order to generate preprocessed signal samples for each of the gas sensors;

a feature extraction processor configured for receiving the preprocessed signal samples and for extracting one or more feature values from the received preprocessed signal samples of each of the gas sensors based on characteristics of each received preprocessed signal samples of the respective gas sensor; and a gas concentration processor for creating for each of the gas sensors a sensing result, wherein the gas concentration processor comprises a classification processor configured for receiving a first group of the one or more feature values comprising feature values for each of the gas sensors, wherein the classification processor is configured for outputting a class decision value for each of the gases, wherein each of the class decision values indicate whether the respective gas is present in the mixture of gases, wherein the classification processor is configured for outputting a confidence value for each of the class decision values, wherein each of the confidence values indicates a reliability of a respective class decision value, wherein the classification processor comprises a first trained model based algorithm processor and a first trained model for the first trained model based algorithm processor, wherein one or more feature values of the first group are fed to different inputs of the first trained model based algorithm processor, and wherein each of the class decision values and each of the confidence values are provided on different outputs of the first trained model based algorithm processor, wherein the gas concentration processor comprises a quantification processor configured for receiving a second group of the feature values comprising feature values for each of the gas sensors and for creating for each of the gases an estimation value, wherein each of the estimation values indicates a quantitative estimation of a concentration of the respective gas, wherein the quantification processor comprises a second trained model based algorithm processor and a second trained model for the second trained model based algorithm processor, wherein the feature values of the second group are fed to different inputs of the second trained model based algorithm processor, wherein the estimation values for the gases are provided on different outputs of the second trained model based algorithm processor, and wherein the gas concentration processor is configured in such way that the sensing result for each of the gases depends on the estimation value for the respective gas, on the class decision value for the respective gas and on the confidence value for the respective gas.

2. The gas sensing device according to claim 1, wherein the one or more chemo-resistive gas sensors are alternately operated in recovery phases and in sense phases, and wherein the one or more heat sources are controlled in such way that the one or more chemo-resistive gas sensors are each heated according to one or more first temperature profiles of the one or more temperature profiles during the recovery phases and according to one or more second temperature profiles of the one or more temperature profiles during the sense phases, wherein for each of the gas sensors a maximum temperature of the respective first temperature profile is higher than a maximum temperature of the respective second temperature profile.

3. The gas sensing device according to claim 1, wherein the preprocessing processor is configured for executing a baseline calibration algorithm for the signal samples received from the one or more chemo-resistive gas sensors.

4. The gas sensing device according to claim 1, wherein the preprocessing processor is configured for executing a filtering algorithm for the signal samples received from the one or more chemo-resistive gas sensors.

5. The gas sensing device according to claim 1, wherein the feature extraction processor is configured for extracting from the received preprocessed signal samples a normalized sensor sensitivity as one of the one or more feature values for each of the gas sensors.

6. The gas sensing device according to claim 1, wherein the feature extraction processor is configured for extracting from the received preprocessed signal samples a slope of one of the preprocessed signal samples as one of the one or more feature values for each of the gas sensors.

7. The gas sensing device according to claim 1, wherein the feature extraction processor is configured for extracting from the received preprocessed signal samples for each of the gas sensors a time correlation between a first of the preprocessed signal samples of the respective gas sensor and a second preprocessed signal sample of the respective gas sensor as one of the one or more feature values for the respective gas sensor.

8. The gas sensing device according to claim 1, wherein the feature extraction processor is configured for extracting from the received preprocessed signal samples for each of the gas sensors a spatial correlation between one of the preprocessed signal samples of the respective gas sensor and one of the preprocessed signal sample of another of the gas sensors as one of the one or more feature values for the respective gas sensor.

9. The gas sensing device according to claim 1, wherein the first trained model based algorithm processor is implemented as a first artificial neural network.

10. The gas sensing device according to claim 1, wherein the second trained model based algorithm processor is implemented as a second artificial neural network.

11. The gas sensing device according to claim 1, wherein for each of the gases the sensing result for the respective gas is the estimation value for the respective gas, wherein the class decision value for the respective gas and the confidence value for the respective gas are fed to one of the inputs of the second trained model based algorithm processor in order to make the estimation value for each of the gases dependent on the class decision value for the respective gas and on the confidence value for the respective gas.

12. The gas sensing device according to claim 1, wherein the gas concentration processor comprises a post processing processor configured for estimating the sensing result for each of the gas sensors depending on the estimation value for the respective gas sensor, on the class decision value for the respective gas sensor and on the confidence value for the respective sensor based on one or more predefined rules.

13. The gas sensing device according to claim 12, wherein the post processing processor is configured for re-calibration of each of the gas sensors using the estimation value for the respective gas sensor, the class decision value for the respective gas sensor and the confidence value for the respective gas sensor.

14. The gas sensing device according to claim 1, wherein the gas concentration processor comprises a feature normalization processor configured for receiving the second group of the one or more feature values, the class decision values for each of the gases and the confidence values for each of the gases, wherein the feature normalization processor is configured for calculating a normalized form of the second group of the one or more feature values using the class decision values for each of the gases and the confidence values for each of the gases, wherein the feature normalization processor is configured for transmitting the second group of the one or more feature values in the normalized form to the quantification processor.

15. The gas sensing device according to claim 1, wherein the second trained model based algorithm processor comprises for each of the gases a convolutional processor, wherein the second trained model based algorithm processor comprises a dense layer processor, wherein at least a portion of the second group of the one or more feature values is fed to each of the convolutional processors, wherein each of the convolutional processors is configured for creating for each of the gases a preliminary estimation value, wherein each of the preliminary estimation values indicates a quantitative preliminary estimation of a concentration of the respective gas, wherein the preliminary estimation value for each of the gases, the class decision value for each of the gases and the confidence value for each of the gases are input to the dense layer processor, wherein the dense layer processor creates the estimation value for each of the gases based on the preliminary estimation values, based on the class decision values and based on the confidence values.

16. A method for operating a gas sensing device, the method comprising:
using one or more gas sensors for generating signal samples corresponding to a concentration of one of one or more gases in a mixture of gases;
using one or more heat sources for heating each of the gas sensors according to one or more temperature profiles;
using a preprocessing processor for receiving the signal samples from each of the gas sensors and for preprocessing the received signal samples in order to generate preprocessed signal samples for each of the gas sensors;
using a feature extraction processor for receiving the preprocessed signal samples and for extracting one or more feature values from the received preprocessed signal samples of each of the gas sensors based on characteristics of the received preprocessed signal samples of the one or more respective sensors;
using a classification processor of a gas concentration processor for receiving a first group of the one or more feature values comprising feature values for each of the gas sensors, wherein the classification processor is configured for outputting a class decision value for each of the gases, wherein each of the class decision values indicate whether the respective gas is present in the mixture of gases, wherein the classification processor is configured for outputting a confidence value for each of the class decision values, wherein each of the confidence values indicates a reliability of a respective class decision value, wherein the classification processor comprises a first trained model based algorithm processor and a first trained model for the first trained model based algorithm processor, wherein one or more feature values of the first group are fed to different inputs of the first trained model based algorithm processor, and wherein each of the class decision values and each of the confidence values are provided on different outputs of the first trained model based algorithm processor;
using a quantification processor of the gas concentration processor for receiving a second group of the one or more feature values comprising feature values for each of the gas sensors and for creating for each of the gases an estimation value, wherein each of the estimation values indicates a quantitative estimation of a concentration of the respective gas, wherein the quantification processor comprises a second trained model based algorithm processor and a second trained model for the second trained model based algorithm processor, wherein the one or more feature values of the second group are fed to different inputs of the second trained model based algorithm processor, wherein the estimation values for the gases are provided on different outputs of the second trained model based algorithm processor; and
using the gas concentration processor in such way that the sensing result for each of the gases depends on the estimation value for the respective gas, on the class decision value for the respective gas and on the confidence value for the respective gas.

17. The method according to claim 16, wherein the first trained model based algorithm processor is implemented as a first artificial neural network.

18. The method according to claim 16, wherein the second trained model based algorithm processor is implemented as a second artificial neural network.

19. A gas sensing system configured for:
using a gas sensor for generating signal samples corresponding to a concentration of one of a gas in a mixture of gases;
using a heat sources for heating the gas sensor according to a temperature profile;
using a preprocessing processor for receiving the signal samples from the gas sensor and for preprocessing the signal samples to generate first signal samples;
using a feature extraction processor for receiving the first signal samples and for extracting a feature value from the first signal samples based on characteristics of the first signal samples;
using a classification processor of a gas concentration processor for receiving a first group of the feature values, wherein the classification processor is configured for outputting a class decision value for the gas, wherein the class decision value indicates whether the gas is present in the mixture of gases, wherein the classification processor is configured for outputting a confidence value for the class decision value, wherein the classification processor comprises a first algorithm processor and a first trained model, wherein the feature values of the first group are fed to inputs of the first algorithm processor, and wherein the class decision value and the confidence value are provided on outputs of the first algorithm processor;
using a quantification processor of the gas concentration processor for receiving a second group of the feature values and for creating an estimation value for the gas, wherein the estimation value indicates a quantitative estimation of a concentration of the gas, wherein the quantification processor comprises a second algorithm processor and a second trained model, wherein the feature values of the second group are fed to inputs of the second algorithm processor, wherein the estimation values for the gas are provided on outputs of the second algorithm processor; and using the gas concentration processor such that a measured concentration for the gas depends on the estimation value for the gas, on the class decision value for the gas, and on the confidence value for the gas.

20. The gas sensing system according to claim 19, wherein the first algorithm processor is implemented as a first artificial neural network, and wherein the second algorithm processor is implemented as a second artificial neural network.

* * * * *

UNITED STATES PATENT AND TRADEMARK OFFICE
CERTIFICATE OF CORRECTION

PATENT NO. : 11,971,397 B2
APPLICATION NO. : 17/361853
DATED : April 30, 2024
INVENTOR(S) : Carbonelli et al.

It is certified that error appears in the above-identified patent and that said Letters Patent is hereby corrected as shown below:

In the Claims

In Column 21, in Claim 16, Line 55, after "respective" insert -- gas --.

Signed and Sealed this
Fourth Day of June, 2024

Katherine Kelly Vidal
*Director of the United States Patent and Trademark Office*